US00PP34573P2

(12) United States Plant Patent
Graff

(10) Patent No.: US PP34,573 P2
(45) Date of Patent: Sep. 13, 2022

(54) POINSETTIA PLANT NAMED 'QS47'

(50) Latin Name: ***Euphorbia pulcherrima* Willd.**
Varietal Denomination: QS47

(71) Applicant: Poul Graff, Sabro (DK)

(72) Inventor: Poul Graff, Sabro (DK)

(73) Assignee: GRAFF BREEDING A/S, Sabro (DK)

( * ) Notice: Subject to any disclaimer, the term of this patent is extended or adjusted under 35 U.S.C. 154(b) by 0 days.

(21) Appl. No.: 17/694,397

(22) Filed: Mar. 14, 2022

(51) Int. Cl.
*A01H 5/02* (2018.01)
*A01H 6/38* (2018.01)

(52) U.S. Cl.
USPC ..... Plt./305
CPC ..... *A01H 6/385* (2018.05)

(58) Field of Classification Search
USPC ..... Plt./305
CPC ..... A01H 6/385; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of Poinsettia plant named 'QS47', characterized by its compact, upright and uniformly mounding plant habit; moderately vigorous growth habit; freely branching habit; dark green-colored leaves; dense inflorescences with numerous curly and yellow-colored flower bracts; and excellent post-production longevity.

1 Drawing Sheet

Botanical designation: *Euphorbia pulcherrima* Willd.
Cultivar denomination: 'QS47'.

STATEMENT REGARDING PRIOR DISCLOSURES BY INVENTOR/APPLICANT & ASSIGNEE

An European Community Plant Breeder's Rights application for the instant plant was filed by the Applicant/Assignee of the instant application, Graff Breeding A/S of Sabro, Denmark on Nov. 26, 2021, application number 2021/3055. Foreign priority is not claimed to this European Plant Breeder's Rights application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of Poinsettia plant, botanically known as *Euphorbia pulcherrima* Willd. and hereinafter referred to by the name 'QS47'.

The new Poinsettia plant is a product of a planned breeding program conducted by the Inventor in Sabro, Denmark The objective of the breeding program is to create uniform and freely-branching Poinsettia plants with attractive inflorescences and good postproduction longevity.

The new Poinsettia plant originated from an open-pollination in August, 2016 in Sabro, Denmark of a proprietary selection of *Euphorbia pulcherrima* Willd. identified as code number QS-17, not patented, as the female, or seed, parent with unknown selection of *Euphorbia pulcherrima* Willd. as the male, or pollen, parent. The new Poinsettia plant was discovered and selected by the Inventor as a single flowering plant within the progeny of the stated open-pollination in a controlled greenhouse environment in Sabro, Denmark in May, 2017.

Asexual reproduction of the new Poinsettia plant by terminal vegetative cuttings in a controlled greenhouse environment in Sabro, Denmark since September, 2017 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'QS47'. These characteristics in combination distinguish 'QS47' as a new and distinct Poinsettia plant:

1. Compact, upright and uniformly mounding plant habit.
2. Moderately vigorous growth habit.
3. Freely branching habit.
4. Dark green-colored leaves.
5. Dense inflorescences with numerous curly and yellow-colored flower bracts.
6. Excellent post-production longevity.

Plants of the new Poinsettia can be compared to plants of the female parent selection. In side-by-side comparisons, plants of the new Poinsettia differ primarily from plants of the female parent selection in cyathia development as plants of the new Poinsettia produce fewer cyathia per inflorescence than plants of the female parent selection.

Plants of the new Poinsettia can also be compared to plants of *Euphorbia pulcherrima* Willd. 'Q104', disclosed in U.S. Plant Pat. No. 30,719. In side-by-side comparisons, plants of the new Poinsettia differ primarily from plants of 'Q104' in the following characteristics:

1. Plants of the new Poinsettia have slightly shorter flower bracts than plants of 'Q104'.
2. Flower bracts of plants of the new Poinsettia are curly whereas flower bracts of 'Q104' are mostly flat.
3. Flower bracts of plants of the new Poinsettia are darker yellow in color than flower bracts of plants of 'Q104'.

BRIEF DESCRIPTION OF THE PHOTOGRAPH

The accompanying photograph illustrates the overall appearance of the new Poinsettia plant showing the colors as true as it is reasonably possible to obtain in colored reproductions of this type. Colors in the photograph may differ slightly from the color values cited in the detailed botanical description which accurately describe the colors of the new Poinsettia plant. The photograph is a side perspective view of a typical flowering plant of 'QS47' grown in a container.

DETAILED BOTANICAL DESCRIPTION

The aforementioned photograph and following observations, measurements and values describe plants grown during the winter in 13-cm containers in a glass-covered greenhouse in Sabro, Denmark and under cultural practices typical of commercial Poinsettia production. During the production of the plants, day temperatures averaged 18° C., night temperatures ranged from 16° C. to 18° C. and light levels ranged from 40 to 50 klux. Plants were pinched one time eight weeks after planting and plants were 25 weeks old when the photograph and the description were taken. In the description, color references are made to The Royal Horticultural Society Colour Chart, 2001 Edition, except where general terms of ordinary dictionary significance are used.

Botanical classification: *Euphorbia pulcherrima* Willd. 'QS47'.

Parentage:

*Female, or seed, parent.*—Proprietary selection of *Euphorbia pulcherrima* Willd. identified as code number QS-17, not patented.

*Male, or pollen, parent.*—Unknown selection of *Euphorbia pulcherrima* Willd., not patented.

Propagation:

*Type.*—Terminal vegetative cuttings.

*Time to initiate roots, summer.*—About three weeks at ambient and substrate temperatures about 24° C.

*Time to initiate roots, winter.*—About four weeks at ambient and substrate temperatures about 24° C.

*Time to produce a rooted young plant, summer.*—About eight weeks at ambient and substrate temperatures about 24° C.

*Time to produce a rooted young plant, winter.*—About ten weeks at ambient and substrate temperatures about 24° C.

*Root description.*—Medium in thickness, fleshy; color, close to 161D, actual color of the roots is dependent on substrate composition, water quality, fertilizer type and formulation, substrate temperature and physiological age of roots.

*Rooting habit.*—Freely branching; dense.

Plant description:

*Plant and growth habit.*—Compact, upright and uniformly mounded plant habit; inverted triangle with rounded crown; large full inflorescences positioned above the foliar plane; moderately vigorous growth habit and moderate growth rate.

*Plant height, soil level to top of foliar plane.*—About 15 cm to 25 cm.

*Plant height, soil level to top of floral plane.*—About 15 cm to 30 cm.

*Plant diameter or spread.*—About 20 cm to 40 cm.

*Lateral branch description.*—Branching habit: Freely branching habit, about three to five lateral branches develop after pinching. Length: About 18 cm to 30 cm. Diameter: About 5 mm to 8 mm. Internode length: About 1 cm to 4 cm. Strength: Strong. Texture and luster: Smooth, glabrous; semi-glossy; becoming woody with subsequent development. Angle: Mostly upright to outwardly slanted. Color, developing: Close to 144A. Color, developed: Close to 138A; when woody, becoming closer to 197A.

*Leaf description.*—Arrangement and appearance: Alternate, simple. Length: About 10 cm to 15 cm. Width: About 8 cm to 12 cm. Shape: Broadly ovate. Apex: Aristate. Base: Obtuse, rounded. Margin: Entire, relatively deeply lobed. Venation pattern: Pinnate, reticulate. Texture and luster, upper and lower surfaces: Rugose, glabrous; leathery; matte. Color: Developing leaves, upper surface: Close to 137A. Developing leaves, lower surface: Close to 138B. Fully expanded leaves, upper surface: Close to 139A; venation, close to 139C. Fully expanded leaves, lower surface: Close to 147B; venation, close to 147C. Petioles: Length: About 2 cm to 4 cm. Diameter: About 4 mm to 6 mm. Strength: Strong. Texture and luster, upper and lower surfaces: Smooth, glabrous; semi-glossy. Color, upper surface: Close to 146B. Color, lower surface: Close to 146C.

Inflorescence description:

*Inflorescence type and habit.*—Inflorescences are compound corymbs of cyathia with yellow-colored flower bracts subtending the cyathia; one inflorescence per lateral branch with inflorescences positioned above and beyond the foliar plane.

*Fragrance.*—None detected.

*Natural flowering season.*—Plants flower naturally during the autumn and winter under long nyctoperiod conditions; inflorescence initiation and development can be induced under artificial long nyctoperiod conditions; early flowering habit, response time is about nine weeks after start of long nyctoperiod conditions.

*Post-production longevity.*—Excellent post-production longevity; plants of the new Poinsettia maintain good substance and bract color for about six to eight weeks under interior conditions; flower bracts persistent.

*Inflorescence diameter (including flower bracts).*—About 12 cm to 15 cm.

*Inflorescence height (including flower bracts).*—About 4 cm to 6 cm.

*Flower bracts.*—Quantity per inflorescence: About 12 to 18. Length: About 6 cm to 9 cm. Width: About 8 cm to 11 cm. Shape: Ovate, curly. Apex: Cuspidate. Base: Cordate. Margin: Entire and lobed. Venation:

Pinnate. Texture and luster, upper and lower surfaces: Rugose, glabrous; matte. Aspect: Mostly horizontal to slightly drooping. Color: Developing bracts, upper surface: Close to 144A. Developing bracts, lower surface: Close to 146C. Transitional bracts, upper surface: Close to 139B and 1B. Transitional bracts, lower surface: Close to 146B. Fully expanded bracts, upper surface: Close to 8B; color does not change with subsequent development. Fully expanded bracts, lower surface: Close to 8C; color does not change with subsequent development. Flower bract petioles: Length: About 5 mm to 15 mm. Diameter: About 4 mm to 6 mm. Texture, upper and lower surfaces: Smooth, glabrous. Color, upper surface: Close to 144A. Color, lower surface: Close to 144B.

*Cyathia.*—Quantity per corymb: About five to ten. Length: About 4 mm to 8 mm. Width: About 4 mm to 6 mm. Shape: Rounded to ovate. Texture, inner and outer surfaces: Smooth, glabrous. Color, developing, inner surface: Close to 145C. Color, developing, outer surface: Close to 144A to 144B. Color, fully developed, inner surface: Close to 145C. Color, fully developed, outer surface: Close to 138B and towards the apex, close to 1B. Nectaries: Quantity per cyathium: If present, typically one or two. Length: About 3 mm to 6 mm. Diameter: About 2 mm to 6 mm. Shape: Fan-shaped. Texture, inner and outer surfaces: Smooth, glabrous. Color: When developing, inner surface: Close to 145B. When developing, outer surface: Close to 145A. Fully developed, inner surface: Close to 15A. Fully developed, outer surface: Close to 15B.

*Peduncles.*—Length: About 3 mm to 5 mm. Diameter: About 2 mm to 5 mm. Strength: Strong. Aspect: Mostly upright. Texture and luster: Smooth, glabrous; semi-glossy. Color: Close to 144B.

*Reproductive organs.*—Stamens: Quantity per cyathium: About 50. Filament length: About 3 mm to 5 mm. Filament color: Close to 157A. Anther shape: Reniform. Anther length: About 1 mm. Anther color: Close to 162B. Amount of pollen: Moderate. Pollen color: Close to 11A. Pistils: To date, pistil development has not been observed on plants of the new Poinsettia.

*Seeds and fruits.*—To date, seed and fruit development has not been observed on plants of the new Poinsettia.

Pathogen & pest resistance: To date, plants of the new Poinsettia have not been shown to be resistant to pathogens and pests common to Poinsettia plants.

Temperature tolerance: Plants of the new Poinsettia have been observed to tolerate temperatures ranging from about 12° C. to about 35° C.

It is claimed:

1. A new and distinct Poinsettia plant named 'QS47' as illustrated and described.

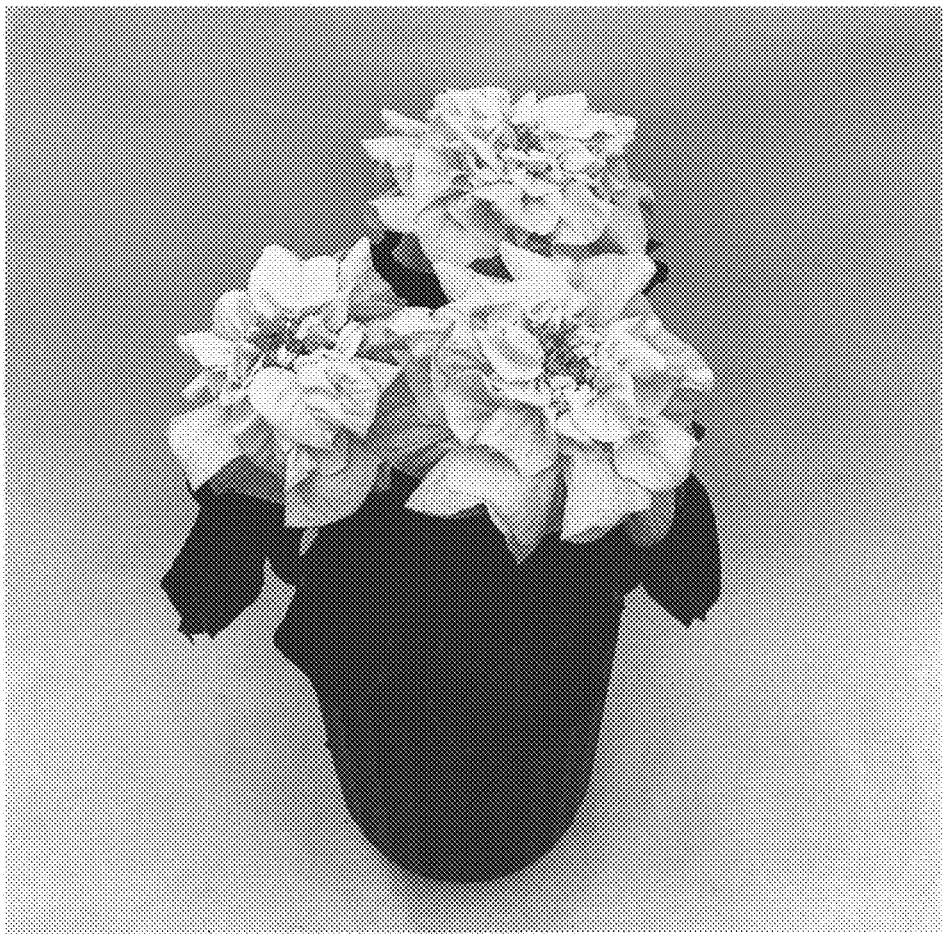

* * * * *